(12) United States Patent
Sur

(10) Patent No.: US 10,405,581 B2
(45) Date of Patent: Sep. 10, 2019

(54) GAS SENSING FOR AN AEROSOL DELIVERY DEVICE

(71) Applicant: RAI STRATEGIC HOLDINGS, INC., Winston-Salem, NC (US)

(72) Inventor: Rajesh Sur, Winston-Salem, NC (US)

(73) Assignee: RAI Strategic Holdings, Inc., Winston-Salem, DC (US)

( * ) Notice: Subject to any disclaimer, the term of this patent is extended or adjusted under 35 U.S.C. 154(b) by 204 days.

(21) Appl. No.: 15/455,338

(22) Filed: Mar. 10, 2017

(65) Prior Publication Data

US 2018/0007970 A1 Jan. 11, 2018

Related U.S. Application Data

(63) Continuation-in-part of application No. 15/205,872, filed on Jul. 8, 2016, now abandoned.

(51) Int. Cl.
*A61M 15/06* (2006.01)
*A24F 47/00* (2006.01)
(Continued)

(52) U.S. Cl.
CPC ......... *A24F 47/008* (2013.01); *A61M 11/042* (2014.02); *G01N 33/0036* (2013.01); *H05B 1/0244* (2013.01); *A61M 15/06* (2013.01); *A61M 2016/0021* (2013.01); *A61M 2205/18* (2013.01); *A61M 2205/3303* (2013.01); *A61M 2205/3306* (2013.01); *A61M 2205/3317* (2013.01);
(Continued)

(58) Field of Classification Search
None
See application file for complete search history.

(56) References Cited

U.S. PATENT DOCUMENTS 1,771,366 A 7/1930 Wyss et al.
2,057,353 A 10/1936 Whittemore, Jr.
(Continued)

FOREIGN PATENT DOCUMENTS

AU 276250 7/1965
CA 2 641 869 5/2010
(Continued)

OTHER PUBLICATIONS

Partial Search Report dated Oct. 9, 2017 in corresponding application No. PCT/IB2017/054020 filed Jul. 3, 2017.
(Continued)

*Primary Examiner* — Thor S Campbell
(74) *Attorney, Agent, or Firm* — Womble Bond Dickinson (US) LLP

(57) ABSTRACT

A control body is coupled or coupleable with a cartridge that is equipped with a heating element and contains an aerosol precursor composition, the control body and cartridge forming an aerosol delivery device. The control body includes a control component to control the heating element to activate and vaporize components of the aerosol precursor composition. The control body also includes a gas sensor configured to detect a presence of gas in an environment of the control body, and the gas sensor or control component are further configured to control operation of at least one functional element of the aerosol delivery device in response to the presence of gas so detected.

18 Claims, 3 Drawing Sheets

(51) Int. Cl.
  *G01N 33/00* (2006.01)
  *H05B 1/02* (2006.01)
  *A61M 11/04* (2006.01)
  *G01N 21/3504* (2014.01)
  *G01N 27/66* (2006.01)
  *A61M 16/00* (2006.01)

(52) U.S. Cl.
  CPC .............. *A61M 2205/3331* (2013.01); *A61M 2205/3553* (2013.01); *A61M 2205/3584* (2013.01); *A61M 2205/3592* (2013.01); *A61M 2205/8206* (2013.01); *G01N 21/3504* (2013.01); *G01N 27/66* (2013.01); *H05B 2203/021* (2013.01); *Y02A 50/25* (2018.01)

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 10,067,108 B2 * | 9/2018 | King-Smith ....... G01N 33/0047 |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2005/0263160 A1 | 12/2005 | Utley et al. |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0192619 A1 | 8/2013 | Tucker et al. |

(56) References Cited

U.S. PATENT DOCUMENTS

| | | |
|---|---|---|
| 2013/0255702 A1 | 10/2013 | Griffith, Jr. et al. |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0007838 A1 | 1/2015 | Fernando et al. |
| 2015/0053217 A1 | 2/2015 | Steingraber et al. |
| 2016/0037826 A1 | 2/2016 | Hearn et al. |
| 2016/0106936 A1 | 4/2016 | Kimmel |
| 2016/0363917 A1* | 12/2016 | Blackley .............. G05B 19/042 |
| 2016/0370335 A1* | 12/2016 | Blackley ............ G01N 33/0013 |
| 2016/0370337 A1* | 12/2016 | Blackley ............ G01N 33/0036 |
| 2017/0224024 A1 | 8/2017 | Jochnowitz et al. |
| 2017/0332702 A1* | 11/2017 | Cameron ............. A61K 9/0073 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | WO 2013/089551 | 6/2013 |
| WO | 2016/062786 A1 | 4/2016 |
| WO | 2016/094225 A1 | 6/2016 |
| WO | 2016/187107 A1 | 11/2016 |
| WO | 2017001520 A1 | 5/2017 |

OTHER PUBLICATIONS

Winsen, "Alcohol Gas Sensor", Model: MQ-3, Manual, Version: 1.3, May 1, 2014, Zhengzhou Winsen Electronics Technology Co., Ltd, pp. 1-7.

Project Lab, "Arduino Breathalyzer: Calibrating the MQ-3 Alcohol Sensor", http://nootropicdesign.com/projectlab/2010/09/17/arduino-breathalyzer, Retrieved Jun. 28, 2016, pp. 1-14.

"MQ-3 Semiconductor Sensor for Alcohol", Jan. 6, 2009, pp. 1-3.

International Search Report dated Feb. 1, 2018 in corresponding International application No. PCT/IB2017/054020 filed Jul. 3, 2017.

\* cited by examiner

GAS SENSING FOR AN AEROSOL DELIVERY DEVICE

CROSS-REFERENCE TO RELATED APPLICATION(S)

The present application is a continuation-in-part of U.S. patent application Ser. No. 15/205,872, entitled: Gas Sensing for an Aerosol Delivery Device, filed on Jul. 8, 2016, the content of which is incorporated herein by reference.

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. Nos. 7,726,320 to Robinson et al. and 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2014/0096781 to Sears et al. and 2014/0283859 to Minskoff et al., as well as U.S. patent application Ser. Nos. 14/282,768 to Sears et al., filed May 20, 2014; 14/286,552 to Brinkley et al., filed May 23, 2014; 14/327,776 to Ampolini et al., filed Jul. 10, 2014; and 14/465,167 to Worm et al., filed Aug. 21, 2014; all of which are incorporated herein by reference.

It would be desirable to provide aerosol delivery devices with functionality for sensing gases within an environment of the aerosol delivery devices.

BRIEF SUMMARY

The present disclosure relates to aerosol delivery devices, methods of forming such devices, and elements of such devices. The present disclosure includes, without limitation, the following example implementations. In some example implementations, a control body coupled or coupleable with a cartridge to form an aerosol delivery device is provided. The cartridge may be equipped with a heating element and contain an aerosol precursor composition. The control body may include a housing, and a control component and gas sensor within the housing. The control component is configured to operate in an active mode in which the control body is coupled with the cartridge. The control component in the active mode is configured to control the heating element to activate and vaporize components of the aerosol precursor composition. The gas sensor is configured to detect a presence of gas in an environment of the control body. The gas sensor or control component are further configured to control operation of at least one functional element of the aerosol delivery device in response to the presence of gas so detected.

In some example implementations of the control body of the preceding or any subsequent example implementation, or any combination thereof, the gas sensor is or includes a photoionization detector (PID) or non-dispersive infrared (NDIR) sensor.

In some example implementations of the control body of any preceding or any subsequent example implementation, or any combination thereof, the gas sensor or control component being further configured to control operation of at least one functional element includes being configured to control an indicator to provide a user-perceptible feedback.

In some example implementations of the control body of any preceding or any subsequent example implementation, or any combination thereof, the gas sensor or control component being further configured to control operation of at least one functional element includes being configured to alter a locked state of the aerosol delivery device.

In some example implementations of the control body of any preceding or any subsequent example implementation, or any combination thereof, the gas sensor being configured to detect the presence of gas includes being configured to detect a concentration of gas in the environment, and the gas sensor or control component being further configured to control operation of the at least one functional element includes being configured to control operation of the at least one functional element in an instance in which the concentration of gas so detected is above a predefined threshold concentration.

In some example implementations of the control body of any preceding or any subsequent example implementation, or any combination thereof, the gas sensor is or includes a photoionization detector (PID) configured to output an ionic current in response to the presence of gas so detected. The control body further comprises a transimpedance amplifier operatively coupled between the PID and control component, and configured to amplify the ionic current. The gas sensor or control component being further configured to control operation of at least one functional element includes the control component being configured to receive and process the ionic current amplified by the transimpedance amplifier, and control the at least one functional element based thereon.

In some example implementations of the control body of any preceding or any subsequent example implementation, or any combination thereof, the gas sensor being configured to detect the presence of gas includes being configured to detect a concentration of gases within a class of gases in the environment of the control body, and the gas sensor or control component being further configured to control operation of the at least one functional element includes being configured to control the at least one functional element based on the concentration of gases so detected.

In some example implementations of the control body of any preceding or any subsequent example implementation, or any combination thereof, the gas sensor or control component being configured to control the at least one functional element based on the concentration of gases includes being configured to identify at least two types of gasses within the class of gases.

In some example implementations of the control body of any preceding or any subsequent example implementation, or any combination thereof, the gas sensor is configured to output a signal in response and corresponding to the concentration of gases, and the control body further comprises a band-pass filter operatively coupled between the gas sensor and control component, and configured to receive the signal and pass only a portion of the signal corresponding to a concentration of a particular gas within the class of gases. The gas sensor or control component being further configured to control operation of at least one functional element includes the control component being configured to receive and process the portion of the signal passed by the band-pass filter, and control the at least one functional element based thereon.

In some example implementations of the control body of any preceding or any subsequent example implementation, or any combination thereof, a communication interface configured to transmit information related to the presence of gas so detected to an external device.

In some example implementations, a cartridge coupled or coupleable with a control body to form an aerosol delivery device is provided. The control body may be equipped with a control component. The cartridge may include a housing defining a reservoir configured to retain aerosol precursor composition, a heating element, and a gas sensor. The heating element is configured to operate in an active mode in which the cartridge is coupled with the control body, and the heating element in the active mode is controllable by the control component to activate and vaporize components of the aerosol precursor composition. The gas sensor is configured to detect a presence of gas in an environment of the control body, and the gas sensor or control component are further configured to control operation of at least one functional element of the aerosol delivery device in response to the presence of gas so detected.

In some example implementations of the cartridge of the preceding or any subsequent example implementation, or any combination thereof, the gas sensor is or includes a photoionization detector (PID) or non-dispersive infrared (NDIR) sensor.

In some example implementations of the cartridge of any preceding or any subsequent example implementation, or any combination thereof, the gas sensor or control component being further configured to control operation of at least one functional element includes being configured to control an indicator to provide a user-perceptible feedback.

In some example implementations of the cartridge of any preceding or any subsequent example implementation, or any combination thereof, the gas sensor or control component being further configured to control operation of at least one functional element includes being configured to alter a locked state of the aerosol delivery device.

In some example implementations of the cartridge of any preceding or any subsequent example implementation, or any combination thereof, the gas sensor being configured to detect the presence of gas includes being configured to detect a concentration of gas in the environment, and the gas sensor or control component being further configured to control operation of the at least one functional element includes being configured to control operation of the at least one functional element in an instance in which the concentration of gas so detected is above a predefined threshold concentration.

In some example implementations of the cartridge of any preceding or any subsequent example implementation, or any combination thereof, the gas sensor is or includes a photoionization detector (PID) configured to output an ionic current in response to the presence of gas so detected, and the cartridge further comprises a transimpedance amplifier operatively coupled between the PID and control component, and configured to amplify the ionic current. The gas sensor or control component being further configured to control operation of at least one functional element includes the control component being configured to receive and process the ionic current amplified by the transimpedance amplifier, and control the at least one functional element based thereon.

In some example implementations of the cartridge of any preceding or any subsequent example implementation, or any combination thereof, the gas sensor being configured to detect the presence of gas includes being configured to detect a concentration of gases within a class of gases in the environment of the cartridge, and the gas sensor or control component being further configured to control operation of the at least one functional element includes being configured to control the at least one functional element based on the concentration of gases so detected.

In some example implementations of the cartridge of any preceding or any subsequent example implementation, or any combination thereof, the gas sensor or control component being configured to control the at least one functional element based on the concentration of gases includes being configured to identify at least two types of gasses within the class of gases.

In some example implementations of the cartridge of any preceding or any subsequent example implementation, or any combination thereof, the gas sensor is configured to output a signal in response and corresponding to the concentration of gases, and the cartridge further comprises a band-pass filter operatively coupled between the gas sensor and control component, and configured to receive the signal and pass only a portion of the signal corresponding to a concentration of a particular gas within the class of gases. The gas sensor or control component being further configured to control operation of at least one functional element includes the control component being configured to receive and process the portion of the signal passed by the band-pass filter, and control the at least one functional element based thereon.

In some example implementations of the cartridge of any preceding or any subsequent example implementation, or any combination thereof, the control body comprises a communication interface operatively coupled to the control component and configured to transmit information related to the presence of gas so detected to an external device.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
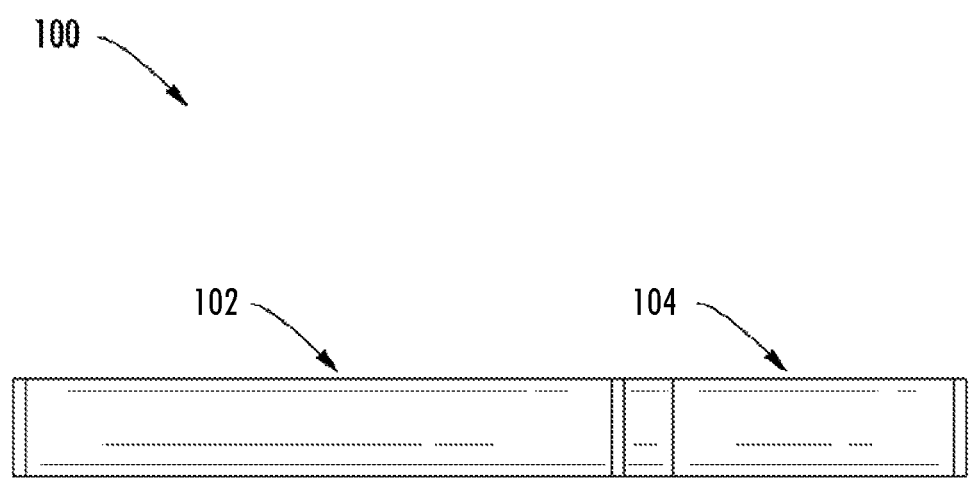
FIG. 1 illustrates a side view of an aerosol delivery device including a cartridge coupled to a control body according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or supercapacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

In various examples, an aerosol delivery device can comprise a reservoir configured to retain the aerosol precursor composition. The reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material a cellulose acetate material, a carbon material, a polyethylene terephthalate (PET) material, a rayon material, or an organic cotton material can be used. A reservoir may be substantially in the form of a container and may include a fibrous material included therein.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular or rhomboidal in cross-section, which may lend itself to greater compatibility with a substantially flat or thin-film power source or supercapacitor, such as a power source including a flat battery. The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery, rechargeable battery (e.g., rechargeable thin-film solid state battery) or rechargeable supercapacitor, and thus may be combined with any type of recharging technology, including connection to a typical wall outlet, connection to a car charger (i.e., a cigarette lighter receptacle), connection to a computer, such as through a universal serial bus (USB) cable or connector (e.g., a 2.0, 3.0 or C type USB cable or connector), connection to a photovoltaic cell (sometimes referred to as a solar cell) or solar panel of solar cells, wireless connection to a Radio Frequency (RF), wireless connection to induction-based charging pads, or connection to a RF-to-DC converter. Further, in some example implementations, the cartridge may comprise a single-use cartridge, as disclosed in U.S. Pat. No. 8,910,639 to Chang et al., which is incorporated herein by reference in its entirety.

Figure 2:
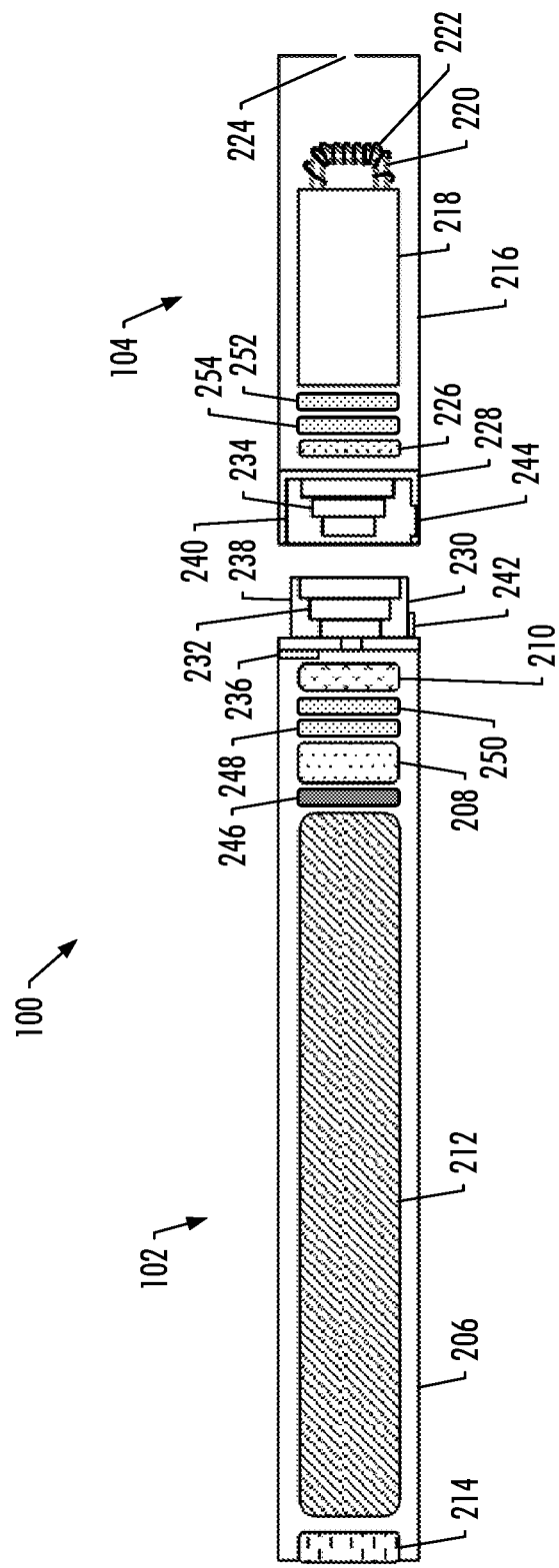
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG. 2 are representative of the components that may be present in a control body and cartridge and are not intended to limit the scope of components that are encompassed by the present disclosure. As shown, for example, the control body can be formed of a control body shell 206 that can include a control component 208 (e.g., a microprocessor, individually or as part of a microcontroller), a flow sensor 210, a power source 212 and one or more light-emitting diodes (LEDs) 214, and such components can be variably aligned. The power source may include, for example, a battery (single-use or rechargeable), lithium-ion battery, solid-state battery (SSB), thin-film SSB, supercapacitor or the like, or some combination thereof. Some examples of a suitable power source are provided in U.S. patent application Ser. No. 14/918,926 to Sur et al., filed Oct. 21, 2015, which is incorporated by reference. The LED (e.g., an organic LED (OLED)) may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED.

The cartridge 104 can be formed of a cartridge shell 216 enclosing a reservoir 218 configured to retain the aerosol precursor composition, and including a heater 222 (sometimes referred to as a heating element). In various configurations, this structure may be referred to as a tank; and accordingly, the terms "cartridge," "tank" and the like may be used interchangeably to refer to a shell or other housing enclosing a reservoir for aerosol precursor composition, and including a heater.

As shown, in some examples, the reservoir 218 may be in fluid communication with a liquid transport element 220 adapted to wick or otherwise transport an aerosol precursor composition stored in the reservoir housing to the heater 222. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be resistive heating element such as a wire coil. Example materials from which the wire coil may be formed include titanium (Ti), platinum (Pt), nichrome (NiCrFe) Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns), silver palladium (AgPd) conductive inks, boron doped silica, and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

An opening 224 may be present in the cartridge shell 216 (e.g., at the mouthend) to allow for egress of formed aerosol from the cartridge 104.

The cartridge 104 also may include one or more electronic components 226, which may include an integrated circuit, a memory component, a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that the control component and the flow sensor may be combined as an electronic circuit board with the air flow sensor attached directly thereto. Further, the electronic circuit board may be positioned horizontally relative the illustration of FIG. 1 in that the electronic circuit board can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference in its entirety. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The aerosol delivery device 100 may be substantially rod-like or substantially tubular shaped or substantially cylindrically shaped in some examples. In other examples, further shapes and dimensions are encompassed—e.g., a rectangular or triangular cross-section, multifaceted shapes, or the like.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a power-source protection circuit configured to detect power-source input, loads on the power-source terminals, and charging input. The power-source protection circuit may include short-circuit protection, under-voltage lock out and/or over-voltage charge protection. The aerosol delivery device may also include components for ambient temperature measurement, and its control component 208 may be configured to control at least one functional element to inhibit power-source charging—particularly of any battery—if the ambient temperature is below a certain temperature (e.g., 0° C.) or above a certain temperature (e.g., 45° C.) prior to start of charging or during charging.

Power delivery from the power source 212 may vary over the course of each puff on the device 100 according to a power control mechanism. The device may include a "long puff" safety timer such that in the event that a user or component failure (e.g., flow sensor 210) causes the device to attempt to puff continuously, the control component 208 may control at least one functional element to terminate the puff automatically after some period of time (e.g., four seconds). Further, the time between puffs on the device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may also contain a sensor chip that measures, in real-time, the amount of aerosol precursor in the reservoir. If the aerosol precursor composition level is substantially low, or the reservoir is empty, the aerosol delivery device may prevent current from being delivered and thereby prevent overheating the heating element. The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source. The aerosol device may also have a mechanical switch or a proximity based sensor switch to activate the heater 222 in lieu of a flow sensor configured to detect the flow of air through the aerosol delivery device and thereby effect activation of the heater.

The various components of an aerosol delivery device according to the present disclosure can be chosen from components described in the art and commercially available. Examples of batteries that can be used according to the disclosure are described in U.S. Pat. App. Pub. No. 2010/0028766 to Peckerar et al., which is incorporated herein by reference in its entirety.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off power to the heater when the aerosol delivery device is not be drawn upon during use, and for turning on power to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al. and U.S. Pat. Pub. Nos. 2013/0008457 to Zheng et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/

0261495 to Novak et al., and U.S. Pat. App. Pub. No. 2014/0261408 to DePiano et al., all of which are incorporated herein by reference in their entireties.

The control component 208 includes a number of electronic components, and in some examples may be formed of a printed circuit board (PCB) that supports and electrically connects the electronic components. The electronic components may include a microprocessor or processor core, and a memory. In some examples, the control component may include a microcontroller with integrated processor core and memory, and may further include one or more integrated input/output peripherals. In some examples, the control component may be coupled to a communication interface 246 to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

In accordance with some example implementations, the control body 102 may include a gas sensor 248 configured to detect a presence of gas in an environment of the control body. Examples of a suitable gas sensor may be or include a photoionization detector (PID), non-dispersive infrared (NDIR) gas sensor, or multiple-pin gas sensor. Examples of suitable PIDs are disclosed in U.S. Pat. Nos. 4,398,152, filed Mar. 2, 1982, to Leveson et al.; 4,429,228, filed May 12, 1981, to Anderson et al.; and 5,561,344, filed Mar. 7, 1995, to Hsi et al., each of which is incorporated herein by reference in its entirety. Examples of suitable NDIR gas sensors are disclosed in U.S. Pat. Nos. 5,444,249, filed Aug. 2, 1994, to Wong et al.; 5,834,777, filed Apr. 23, 1997, to Wong et al.; and 6,469,303, filed May 17, 2000, to Sun et al., each of which is incorporated herein by reference in its entirety. Examples of suitable multiple-pin gas sensors are disclosed in U.S. Pat. No. 6,000,928, filed Dec. 28, 1999, to Sachse et al. which is incorporated herein by reference in its entirety.

Examples of suitable gases that may be detected by the gas sensor 248 include carbon monoxide, oxygen, ammonia fluorine, hydrogen sulfide, methane and other gases not explicitly contemplated herein. In some implementations, the gas sensor may be configured to detect the presence of a gas other than the vapor produced by the heater 222 from the aerosol precursor composition, or the aerosol produced from the vapor. The gas sensor or control component 208 may be configured to control operation of at least one functional element of the aerosol delivery device 100 in response to the presence of gas so detected.

In one specific implementation, the gas sensor 248 being configured to detect the presence of gas in the environment of the control body 102 may include the gas sensor being configured to detect the presence of ethanol (a primary ingredient in alcoholic beverages) in the environment of the control body. In this implementation, the environment of the control body may include the mouth of a user of the aerosol delivery device 100 such that the gas sensor functions as an alcohol sensor. In these examples, the gas sensor may be of any of a number of different types of sensors, such as fuel-cell sensors, semiconductor oxide sensors and the like. One particular example of a suitable semiconductor oxide sensor is the model MQ-3 alcohol gas sensor from Zhengzhou Winsen Electronics Technology Co., Ltd.

Further in these implementations, the gas sensor may be more particularly configured to measure an amount of ethanol in a breath of air to which the sensor is exposed, and generate a corresponding signal that indicates a breath alcohol content (BrAC) from which a blood alcohol content (BAC) is calculable by the gas sensor or control component 208. In these example implementations, the control component or gas sensor may be configured to calculate the BAC based on the BrAC. The BAC may be calculated in any suitable manner. For example, the corresponding signal may provide a measure of BrAC that may be in or converted to parts per million (ppm) and correspondingly milligrams per liter (mg/L) (1 ppm=1 mg/L). The BAC may then be calculated from the BrAC according to the following:

$$\% \; BAC = BrAC \; mg/L \times 0.21$$

The aerosol delivery device 100 may be configured in any of a number of different manners for any of a number of different applications, and in some examples may be user programmable for different applications. More particularly, in some examples, this user-programmability may extend to the range of the gas sensor, the operation of the functional element(s) or the like. As another example, the gas sensor may obtain a measurement and detect the presence of the gas in an instance in which the measurement satisfies a threshold.

Functional element(s) of the aerosol delivery device 100 may be controlled in any of a number of different manners in response to the presence of a detected gas. For example, an indicator 250 (e.g., visual indicator, audio indicator, haptic indicator) may be controlled to provide a user-perceptible feedback (e.g., visual, audible, haptic feedback). As another example, functional element(s) may be controlled to alter a locked state of the aerosol delivery device 100. This may include, for example, disabling one or more components of the aerosol delivery device from operation when the presence of a gas is detected. For example, the gas sensor 248 may detect instances in which the power source 212 (e.g., lithium ion battery) is leaking gas, and the gas sensor or control component 208 may control the at least one functional element to automatically shut off the aerosol delivery device.

Similar functionality may also be used to unlock the aerosol delivery device 100 for active-mode operation and thereby limit active-mode operation to only those instances in which the flow sensor 210 detects a flow of air through the aerosol delivery device, and the gas sensor 248 does not detect the presence of a gas. More particularly, for example, the flow sensor may output an airflow-detection signal in response to detection of a flow of air through at least a portion of the aerosol delivery device, and the gas sensor may output a gas-detection signal in response to the presence of gas. The control component 208 may then be configured to initiate operation in the active mode in response to the presence of the airflow-detection signal, and the absence of the gas-detection signal, and therein control the heating element to activate and vaporize components of the aerosol precursor composition.

In addition to or in lieu of applications involving altering a locked state of the aerosol delivery device 100, the gas sensor 248 may enable an even greater number of applications. In some examples, the range of the gas sensor may be set to enable use of the aerosol delivery device as a warning system. In particular, the gas sensor may be used to detect a concentration of gas in the environment, and at least one functional element may be controlled in an instance in which the concentration of gas is above a predefined threshold or outside a predefined acceptable range. For example, the aerosol delivery device and its gas sensor may be used to detect that the concentration of the gas within the environment is hazardous, and control the indicator 250 to provide a user-perceptible feedback to warn the user. For example, For example, the gas sensor may be configured to measure and indicate a concentration of a gas, and detect when the concentration of the gas is above a predefined threshold or outside an acceptance range. In these instances, the indicator may provide the user-perceptible feedback such as an alarm, buzzer or visual indicator (e.g., LED) to warn the user.

In an implementation in which the gas sensor is configured to detect the presence of alcohol, the control component or gas sensor may be configured to calculate the BAC based on the BrAC, and control operation of the functional element(s) based on the BAC so calculated. The functional element(s) of the control body 102 or the aerosol delivery device 100 may be controlled in any of a number of different manners based on the BrAC or BAC. For example, a display may be configured to provide a visual readout of the BrAC or BAC. Additionally or alternatively, for example, feedback may include a visual, audible and/or haptic notification that the BrAC or BAC is above a predefined threshold. In this regard, the predefined threshold in some examples may correspond to an upper limit at or above which a person is considered too legally impaired to operate a vehicle. In these instances, the indicator may provide the user-perceptible feedback such as an alarm, buzzer, vibration or visual indicator (e.g., LED) to warn the user.

In some examples in which the control body 102 includes a communication interface 246, control of the functional elements 302 may include control of the communication interface to cause the communication interface to enable wireless communication of the concentration of gas in the environment to a remote computing system. For example, Also if the BrAC or BAC exceeds a threshold limit, the information may be transmitted to a remote computing system configured to locate and dispatch a cab to the location of the aerosol delivery device 100, and thereby the user.

As further shown in FIG. 2, in addition to or in lieu of the control body 102, the cartridge may include a gas sensor 252 (e.g., PID, NDIR, multiple-pin electrochemical gas sensor or alcohol sensor), and perhaps also an indicator 254. As before, examples of suitable gases that may be detected by the gas sensor include carbon monoxide, oxygen, ammonia fluorine, hydrogen sulfide, methane, ethanol and other gases not explicitly contemplated herein. Similar to above with respect to the presence of an object, functional element(s) of the aerosol delivery device 100 may be controlled in any of a number of different manners in response to a concentration of the gas being detected. For example, an indicator 250, 254 may be controlled to provide a user-perceptible feedback. Additionally or alternatively, for example, functional element(s) may be controlled to alter a locked state of the aerosol delivery device, such as disabling one or more components of the aerosol delivery device from operation when at least a threshold level of a concentration of the gas is detected.

In any of the foregoing examples, as well as in other examples, the gas sensor 248, 252 or control component 208 may be configured to transmit data (including information related to the presence of the detected gas) to an external device including, for example, a service platform for storage, presentation, analysis or the like. This service platform may include one or more computing devices (e.g., servers), and in some examples, the service platform may provide a cloud computing infrastructure. The aerosol delivery device 100 may communicate with the service platform through its communication interface 246, and possibly one or more networks. This communication may even be less direct with the aerosol delivery device being in communication with a computing device (directly or through one or more networks), which is in turn in communication with the service platform (directly or through one or more networks).

Figure 3:
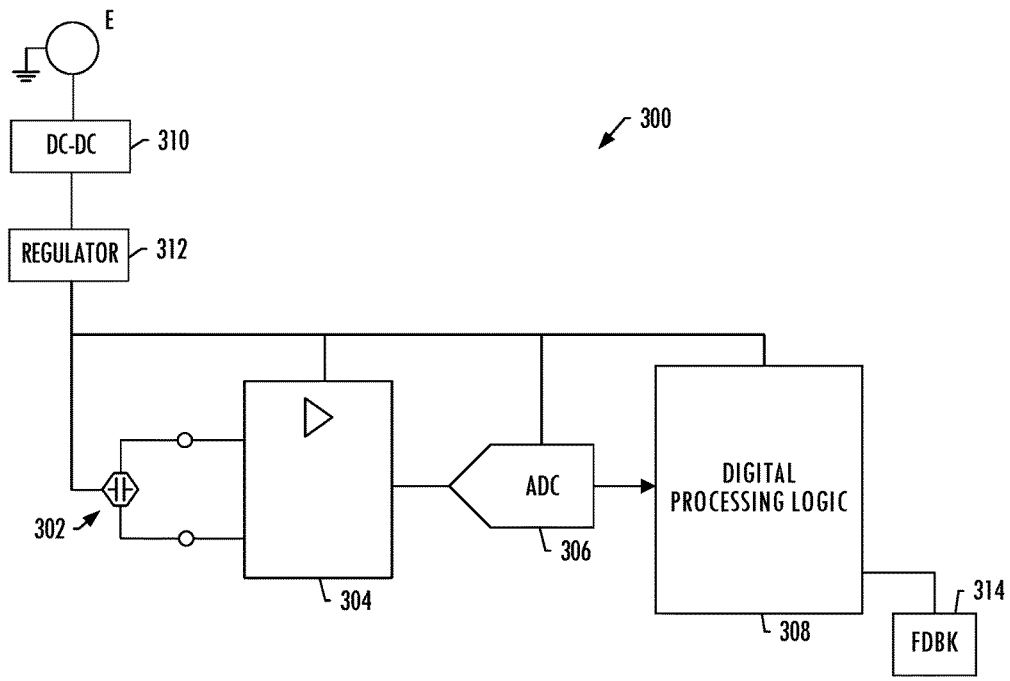
FIGS. 3 and 4 illustrate gas sensors according to various example implementations.

FIG. 3 illustrates a gas sensor 300 that in some examples may correspond to the gas sensor 248, 252 of FIG. 2. As shown, the gas sensor may include a source of energy E configured to power a PID 302. The PID may be configured to detect a gas (e.g., volatile organic compounds), and output an ionic current in response to the presence of the gas so detected. In particular, the volatile organic compounds may be or include aromatics, ketones and/or aldehydes. The PID may, for example, detect acetaldehyde, benzene, ethylbenzene, toluene, and/or xylenes in carbon dioxide.

The source of energy E may also power various other components including, for example, a transimpedance amplifier 304, analog-to-digital-converter (ADC) 306, and/or digital processing logic 308 such as a microprocessor. In some examples, the gas sensor may be at least partially integrated with the control component 208 of the control body 102; and in these examples, the digital processing logic may be or include the control component. The source of energy may be coupled to the various components via a direct current to a direct current (DC-DC) converter 310 and a voltage or current regulator 312 (e.g., linear regulator) respectively configured to regulate a discharge current from the source of energy and maintain a constant output voltage to the other components. The source of energy may be onboard the gas sensor or in some examples may be or include the power source 212 of the control body 102. Similar to the power source, examples of suitable sources of energy include a battery (single-use or rechargeable), lithium ion battery, SSB, thin-film SSB, supercapacitor or the like, or some combination thereof.

The transimpedance amplifier 304 may be operatively coupled between the PID 302 and the ADC 306, and may be configured to amplify the ionic current output by the PID. The amplified ionic current may be provided to an ADC 306 configured to convert the ionic current signal to a corresponding digital signal. This digital signal may be passed to the digital processing logic 308, which may be configured to control operation of at least one functional element in response to the digital signal and thereby the presence of the detected gas. In some examples, the digital processing logic may include the ADC, and thereby be configured to receive and process the ionic current amplified by the transimpedance amplifier, and control the at least one functional element based thereon. This may include, for example, control of an indicator 314, which may also be onboard the gas sensor or separate from but in communication with the gas sensor (e.g., indicator 250).

Figure 4:
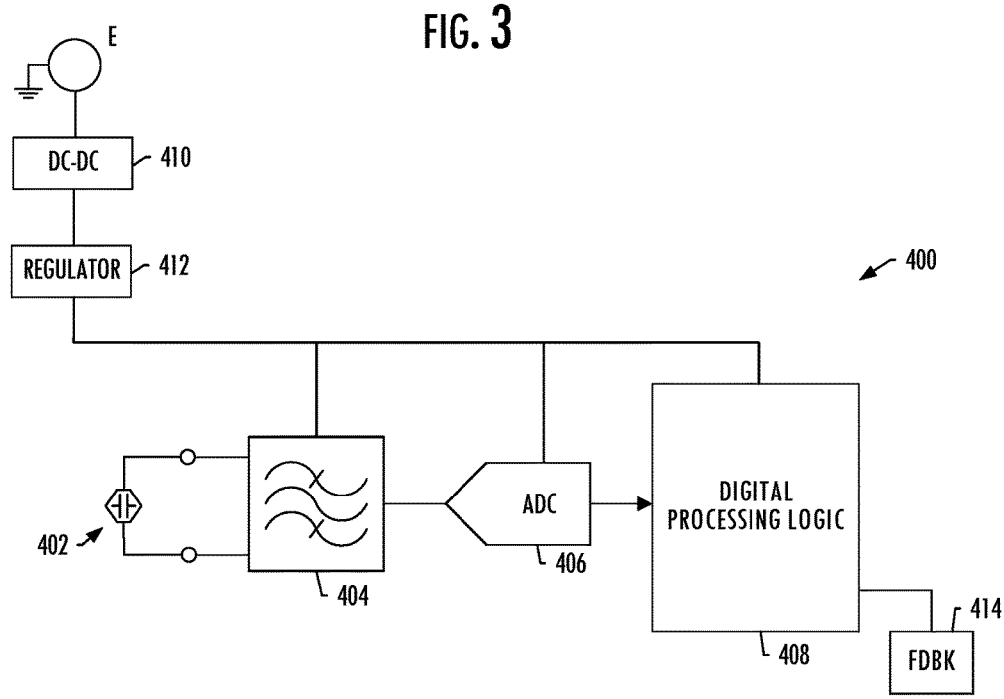

FIG. 4 illustrates a gas sensor 400 that in some examples may correspond to the gas sensor 248, 252 of FIG. 2. In contrast to the gas sensor 300 of FIG. 3, the gas sensor of FIG. 4 may include a NDIR detector 402 and band pass filter 404 instead of respectively a PID 302 and transimpedance amplifier 304. The gas sensor of FIG. 4 may include an ADC 406, digital processing logic 408, DC-DC converter 410 and/or regulator 412 similar to respectively ADC 306, digital processing logic 308, DC-DC converter 310 and/or voltage or current regulator 312 of the gas sensor of FIG. 3. Similar to before, the gas sensor 400 may be at least partially integrated with the control component 208 of the control body 102; and in these examples, the digital processing logic 408 may be or include the control component.

In the gas sensor 400 of FIG. 4, the NDIR detector 402 may be configured to detect and measure concentrations of gases based on absorption of the gas so detected at specific wavelengths, and more particularly, output an infrared signal in response and corresponding to the concentration of gases so detected. In contrast to the PID 302 of FIG. 3, the NDIR may function independent of an external source of energy E. However, the gas sensor may include the source of energy for powering various other components including, for example, the band pass filter 404, ADC 406, and/or digital processing logic 408. The source of energy may be coupled to the various components via the DC-DC converter 410 and regulator 412 (e.g., linear regulator) respectively configured to regulate a discharge current from the source of energy and maintain a constant output voltage to the other components.

In some examples, the gas sensor 400 may be configured to detect a concentration of gases within a class of gases in the environment, and the gas sensor or more particularly its digital processing logic 408 may be configured to control operation of at least one functional element based on the concentration of gases so detected. In some of these examples, controlling the at least one function element may include being configured to identify at least two types of gasses within the class of gases. In particular, the gas sensor may be configured to detect multiple gases at the same instant, and the digital processing logic may be programmed to indicate which of the multiple gases are required for detection within various applications. Further in these examples, the band pass filter 404 may be operatively coupled between the NDIR detector 402 and the ADC 406. The band pass filter may be in turn configured to receive the infrared signal from the NDIR and pass only a portion of the signal corresponding to the concentration of the particular gas. Thus, in some examples, the band-pass filter may have a center frequency that corresponds to a frequency at which a particular gas within the class of gases absorbs light.

In particular, the portion of the signal may be provided to the ADC 406 configured to convert the signal to a corresponding digital signal. This digital signal may be passed to the digital processing logic 408. The gas sensor 400 or more particularly its digital processing logic may be in turn configured to control operation of at least one functional element in response to the digital signal and thereby the presence of the detected gas. In some examples, the digital processing logic may include the ADC, and thereby be configured to receive and process the portion of the infrared signal, and control the at least one functional element based thereon. This may include, for example, control of an indicator 414, which may also be onboard the gas sensor or separate from but in communication with the gas sensor (e.g., indicator 250).

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-4 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A control body coupled or coupleable with a cartridge to form an aerosol delivery device, the cartridge being equipped with a heating element and containing an aerosol precursor composition, the control body comprising:

a housing; and within the housing, a control component configured to operate in an active mode in which the control body is coupled with the cartridge, the control component in the active mode being configured to control the heating element to activate and vaporize components of the aerosol precursor composition; and a gas sensor configured to detect a presence of gas in an environment of the control body, including being configured to detect a concentration of gases within a class of gases in the environment of the control body, wherein the gas sensor or control component is further configured to control operation of at least one functional element of the aerosol delivery device in response to the presence of gas so detected, including being configured to control the at least one functional element based on the concentration of gases so detected.

2. The control body of claim 1, wherein the gas sensor is or includes a photoionization detector (PID) or non-dispersive infrared (NDIR) sensor.

3. The control body of claim 1, wherein the gas sensor or control component being further configured to control operation of at least one functional element includes being configured to control an indicator to provide a user-perceptible feedback.

4. The control body of claim 1, wherein the gas sensor or control component being further configured to control operation of at least one functional element includes being configured to alter a locked state of the aerosol delivery device.

5. The control body of claim 1, wherein the gas sensor being configured to detect the presence of gas includes being configured to detect a concentration of gas in the environment, and wherein the gas sensor or control component being further configured to control operation of the at least one functional element includes being configured to control operation of the at least one functional element in an instance in which the concentration of gas so detected is above a predefined threshold concentration.

6. The control body of claim 1, wherein the gas sensor is or includes a photoionization detector (PID) configured to output an ionic current in response to the presence of gas so detected,
wherein the control body further comprises a transimpedance amplifier operatively coupled between the PID and control component, and configured to amplify the ionic current, and
wherein the gas sensor or control component being further configured to control operation of at least one functional element includes the control component being configured to receive and process the ionic current amplified by the transimpedance amplifier, and control the at least one functional element based thereon.

7. The control body of claim 1, wherein the gas sensor or control component being configured to control the at least one functional element based on the concentration of gases includes being configured to identify at least two types of gasses within the class of gases.

8. The control body of claim 1, wherein the gas sensor is configured to output a signal in response and corresponding to the concentration of gases,
wherein the control body further comprises a band-pass filter operatively coupled between the gas sensor and control component, and configured to receive the signal and pass only a portion of the signal corresponding to a concentration of a particular gas within the class of gases, and
wherein the gas sensor or control component being further configured to control operation of at least one functional element includes the control component being configured to receive and process the portion of the signal passed by the band-pass filter, and control the at least one functional element based thereon.

9. The control body of claim 1 further comprising a communication interface configured to transmit information related to the presence of gas so detected to an external device.

10. A cartridge coupled or coupleable with a control body that is equipped with a control component, the control body being coupled or coupleable with the cartridge to form an aerosol delivery device, the cartridge comprising:
a housing defining a reservoir configured to retain aerosol precursor composition;
a heating element configured to operate in an active mode in which the cartridge is coupled with the control body, the heating element in the active mode being controllable by the control component to activate and vaporize components of the aerosol precursor composition; and
a gas sensor configured to detect a presence of gas in an environment of the control body, including being configured to detect a concentration of gases within a class of gases in the environment of the cartridge,
wherein the gas sensor or control component is further configured to control operation of at least one functional element of the aerosol delivery device in response to the presence of gas so detected, including being configured to control the at least one functional element based on the concentration of gases so detected.

11. The cartridge of claim 10, wherein the gas sensor is or includes a photoionization detector (PID) or non-dispersive infrared (NDIR) sensor.

12. The cartridge of claim 10, wherein the gas sensor or control component being further configured to control operation of at least one functional element includes being configured to control an indicator to provide a user-perceptible feedback.

13. The cartridge of claim 10, wherein the gas sensor or control component being further configured to control operation of at least one functional element includes being configured to alter a locked state of the aerosol delivery device.

14. The cartridge of claim 10, wherein the gas sensor being configured to detect the presence of gas includes being configured to detect a concentration of gas in the environment, and
wherein the gas sensor or control component being further configured to control operation of the at least one functional element includes being configured to control operation of the at least one functional element in an instance in which the concentration of gas so detected is above a predefined threshold concentration.

15. The cartridge of claim 10, wherein the gas sensor is or includes a photoionization detector (PID) configured to output an ionic current in response to the presence of gas so detected,
wherein the cartridge further comprises a transimpedance amplifier operatively coupled between the PID and control component, and configured to amplify the ionic current, and wherein the gas sensor or control component being further configured to control operation of at least one functional element includes the control component being configured to receive and process the ionic current amplified by the transimpedance amplifier, and control the at least one functional element based thereon.

16. The cartridge of claim 10, wherein the gas sensor or control component being configured to control the at least one functional element based on the concentration of gases includes being configured to identify at least two types of gasses within the class of gases.

17. The cartridge of claim 10, wherein the gas sensor is configured to output a signal in response and corresponding to the concentration of gases,
wherein the cartridge further comprises a band-pass filter operatively coupled between the gas sensor and control component, and configured to receive the signal and pass only a portion of the signal corresponding to a concentration of a particular gas within the class of gases, and
wherein the gas sensor or control component being further configured to control operation of at least one functional element includes the control component being configured to receive and process the portion of the signal passed by the band-pass filter, and control the at least one functional element based thereon.

18. The cartridge of claim 10, wherein the control body comprises a communication interface operatively coupled to the control component and configured to transmit information related to the presence of gas so detected to an external device.

* * * * *